Figure 1:
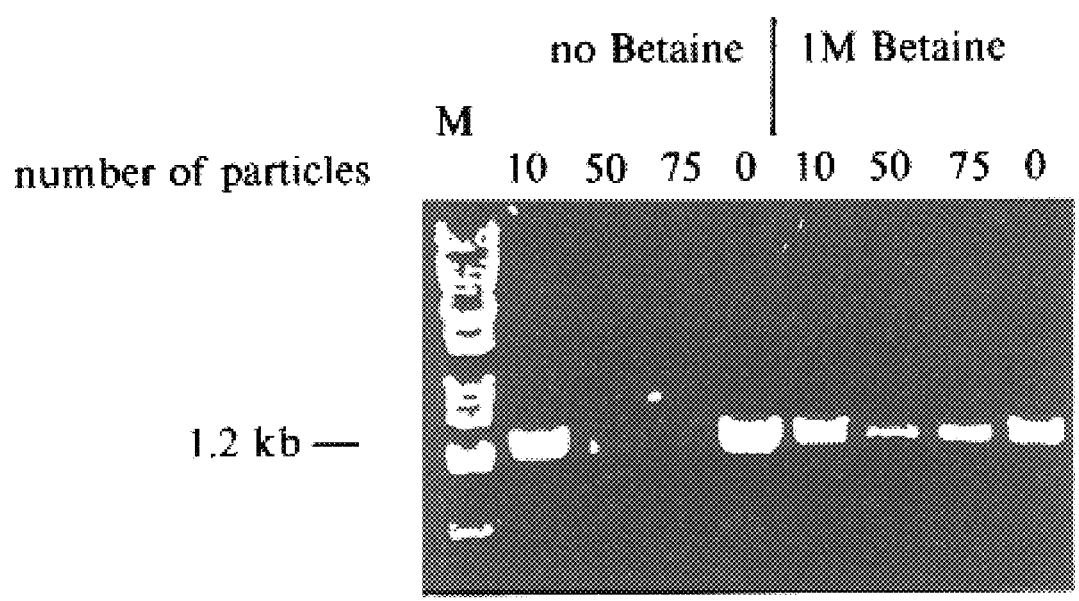

United States Patent [19]
Maier et al.

[11] Patent Number: 6,150,094
[45] Date of Patent: Nov. 21, 2000

[54] USE OF AN OSMOLYTE FOR REDUCING OR ABOLISHING NO-COVALENT INTERACTIONS OF BIOLOGICAL MOLECULES TO INERT SURFACES

[75] Inventors: Elmar Maier, Berlin-Dahlem; Igor Ivanov, Berlin, both of Germany

[73] Assignee: Qiagen GmbH, Hilden, Germany

[21] Appl. No.: 08/862,984

[22] Filed: May 23, 1997

[30] Foreign Application Priority Data

May 23, 1996 [EP] European Pat. Off. .............. 96018278

[51] Int. Cl.[7] ............................ C12Q 1/68; G01N 33/53; G01N 33/567; G01N 33/537
[52] U.S. Cl. ............................ 435/6; 435/91.1; 435/91.2; 435/7.1; 435/7.2; 435/7.92
[58] Field of Search .............................. 435/6, 91.1, 91.2, 435/7.1, 7.2, 7.92

[56] References Cited

U.S. PATENT DOCUMENTS

| | | | |
|---|---|---|---|
| 5,181,999 | 1/1993 | Wiktorowicz | 204/180.1 |
| 5,587,128 | 12/1996 | Wilding et al. | 422/50 |

FOREIGN PATENT DOCUMENTS

| | | | |
|---|---|---|---|
| 0153875 | 9/1985 | European Pat. Off. | G01N 33/543 |
| 0292809 | 11/1988 | European Pat. Off. | G01N 33/543 |
| 0363091 | 4/1990 | European Pat. Off. | G01N 33/569 |
| 0669401 | 8/1995 | European Pat. Off. | C12Q 1/68 |
| 4411588 C1 | 9/1995 | Germany | C12P 19/34 |
| WO 93/22058 | 11/1993 | WIPO | C12Q 1/68 |
| WO 95/20682 | 8/1995 | WIPO | C12Q 1/68 |

OTHER PUBLICATIONS

Moncef Zouali, et al., "A Rapid ELISA For Measurement of Antibodies to Nucleic Acid Antigens Using UV–treated Polystyrene Microplates," *Journal of Immunological Methods*, 90:105–110 (1986).

Thakar, M., et al., "Osmolyte Mediation of T7 DNA Polymerase and Plasmid DNA Stability," *Biochemistry* 33: 12255–12259 (1994).

*Primary Examiner*—Jezia Riley
*Attorney, Agent, or Firm*—Fish & Neave; Jane A. Massaro, Esq.; Elinor Shin

[57] ABSTRACT

The present invention relates to the use of an osmolyte for reducing or abolishing non-covalent interactions of biological molecules to inert surfaces. Furthermore, the present invention relates to kits that may be employed for uses in accordance with the present invention.

17 Claims, 2 Drawing Sheets

USE OF AN OSMOLYTE FOR REDUCING OR ABOLISHING NO-COVALENT INTERACTIONS OF BIOLOGICAL MOLECULES TO INERT SURFACES

This application claims priority under 35 U.S.C. §119 from European patent application Serial No. 96108278.1, filed May 23, 1996.

The present invention relates to the use of an osmolyte for reducing or abolishing non-covalent interactions of biological molecules to inert surfaces. Furthermore, the present invention relates to kits that may be employed for uses in accordance with the present invention.

The development of new materials has had a significant impact on a wide variety of modern technologies. For example, the introduction of e.g. silicon, gallium arsenite or polycrystal materials has in the past strongly propagated the semiconductor technology. In modern biology, similar developments have been observed. Thus, over the past two decades, materials have been established in immunometric methods such as ELISAs that allow for a standardization of experimental protocols and a minimization of material-based error-rates in experimental results. A different but equally important development is concerned with the promotion of novel carrier materials to be used in (column) chromatography for the purification and isolation of biological compounds of interest.

One of the major troubles that scientists have faced in a large number of biological analytical and isolation techniques is that experimental accuracies and production yields may be impaired by background or undesired and possibly unspecific interaction problems. Such problems can arise, for example, by non-covalent binding interactions of proteins or other biological compounds to carrier surfaces. In order to overcome such problems in ELISA techniques, free binding sites on carrier materials such as polystyrrol are "blocked" with unrelated biological materials such as heterologous proteins prior to testing for the compound of interest.

A technology that has in the most recent past revolutionized molecular biology is the PCR technology. Naturally, in view of the wide applicability of PCR, major efforts have been and are presently undertaken to further improve facettes of this technology. One of these efforts is directed to the creation of microreaction volumes of PCR chips, i.e. microfabricated silicon chips bonded to a piece of flat glass to form a PCR reaction chamber; see, e.g., Shoffner et al., "Chip PCR. I. Surface passivation of microfabricated silicon-glass chips for PCR", Nucl. Acids Res. 24 (1996), 375–379. Since native silicon which so far has been used in the production of PCR chips has turned out to be an inhibitor of the PCR, these investigators searched for materials and methods to obtain reliable PCR results unimpaired by such inhibition or background problems. They propose to use an oxidized silicon ($SiO_2$) surface to achieve their goal.

In spite of these achievements, it would be highly desirous and advantageous to find a way of reducing or eliminating non-specific or non-covalent interactions between inert surfaces and biological molecules without having to modify commonly commercially available surfaces or being limited to the use of only a small selection of suitable inert surfaces. A successful development of such a means would, of course, have a wide applicability in modern biology and not be restricted to the use in the PCR technology. For example, Volkmuth and Austin have designed a method for the micro-elelectrophesis of DNA molecules (Volkmuth and Austin, "DNA electrophoresis in microlithographic arrays", Nature 358 (1992), 600–602). Such techniques could also benefit from the inclusion of osmolytes such as betaine into the buffer systems.

Thus, the technical problem underlying the present invention was to overcome the prior art problems detailed hereinabove and develop a system that reduces or eliminates undesired interactions of biological molecules with inert surfaces.

The solution to said technical problem is achieved by providing the embodiments characterized in the claims.

Accordingly, the present invention relates to the use of an osmolyte for reducing or abolishing non-covalent interactions of biological molecules to inert surfaces. In accordance with the present invention, it has surprisingly been found that the addition of an osmolyte in a suitable concentration to a solution comprising a biological molecule will reduce, if not abolish the non-covalent interaction of said molecule with said surface.

Osmolytes (or osmotic solutes) are found in a wide variety of water-stressed prokaryotic and eukaryotic organisms. The three types of osmolyte systems found in all such organisms except for the halobacteria are polyhydric alcohols (such as glycerol and saccharose), free amino acids and their derivatives (such as taurine and β-alanine), and methylamines (e.g. trimethylamine-N-oxide (TMAO), betaine and sarcosine) or combinations of methylamines and urea (see, for a review, Yancey et al., "Living with water stress: evolution of osmolyte systems" Science 217 (1982), 1214–1222).

One of the major advantages of the present invention is that the simple addition of an osmolyte to such a solution conveniently reduces or abolishes the interaction of said molecules with a wide variety of inert surfaces. The special design or selection of an adequate surface for a specific experimental set-up or purpose is therefore no longer necessary, A further advantage of the present invention is that it allows for the simple design of a variety of previously crucial experiments and therefore saves time and costs for the interested investigator.

The term "biological molecule" as used herein refers to organic molecules which are part of an organism or a living cell or derivatives of such molecules. These molecules may be of natural, synthetic or semisynthetic origin.

As used herein, the term "inert" has the meaning of "having little or no ability to chemically react". It therefore bears the same meaning as inertness in connection with nitrogens which occurs uncombined in the atmosphere.

In a preferred embodiment of the use of the present invention said osmolyte is a zwitterionic osmolyte.

In a most preferred embodiment of the use of the present invention said zwitterionic osmolyte has the structural formula

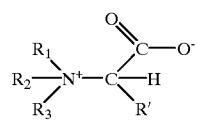

wherein $R_1$, $R_2$ and $R_3$ are H, $CH_3$, $C_2H_5$ or any other alkyl, and R' is any amino acid residue.

In a further most preferred embodiment of the use of the present invention said zwitterionic osmolyte is an amino acid or its methylation product.

In an additional most preferred embodiment of the use of the present invention said zwitterionic osmolyte is betaine and preferably glycine-betaine.

In a further preferred embodiment of the present invention said osmolyte is present at a final concentration of 1 to 2.5 M. The advantageous properties of said osmolyte also emerge, if it is included in the reaction mixture at a lower concentration than 1 M. However, particularly advantageous results are obtained, if the osmolyte is present in a final concentration of 1 to 2.5 M.

In an additional preferred embodiment of the present invention said biological molecule is a macromolecule.

The term "macromolecule" in connection with the term "biological molecule" is perfectly clear to the person skilled in the art and need not be described here any further.

In a most preferred embodiment of the use of the present invention, said macromolecule is a carbohydrate, a polynucleic acid or a polypeptide, or combinations or modifications thereof. Said combinations or modifications need not necessarily have a biological function. In the alternative, their biological function may not be known in the art (yet); see, for example, the discussion about peptide nucleic acids (Nielsen et al., Science 254 (1991), 1497–1500) Yet, said modified biological macromolecules may have essentially the same physico-chemical properties as the biological macromolecules they are derived from and may find the same or similar applications e.g. in molecular biology.

In a further preferred embodiment of the present invention said biological molecule is a peptide or an oligonucleotide or combinations or modifications thereof.

In a most preferred embodiment of the present invention said polynucleic acid or oligonucleotide is DNA. The term "DNA" as used herein includes any type of DNA, in particular cDNA and genomic DNA.

In a further most preferred embodiment of the present invention said polynucleic acid or oligonucleotide is RNA. The term "RNA", as used in the context of the present invention, is intended to mean any type of RNA and in particular mRNA.

In a further preferred embodiment of the present invention said inert surface is a silicon surface, a silicium wafer, a glass surface or combinations or chemical modifications thereof.

Most conveniently, said substance is a manufactured silicon. Said silicon may be obtained e.g., by standard manufacturing or processing techniques such as photolithography.

The present invention additionally relates to a kit comprising at least (a) a concentrated stock solution of an osmolyte as specified herein before;

(b) a reaction buffer formulation containing an osmolyte as specified herein before; and/or (c) an enzyme formulation containing an osmolyte as specified herein before.

The various components of the kit of the present invention are preferably formulated in standard reaction vials and independently of one another. The concentrations used in the stock solutions comprised in the kit of the invention are suitable to allow an appropriate dilution of the osmolyte to be useful in the teachings of the present invention. In the embodiments b) and c) of the buffer of the invention, the osmolyte is preferably contained therein in its final concentration. The ranges and limits of said final concentrations have been provided herein before in the specification.

The figures show:

FIG. 1: PCR In the presence of silicon particles and zwitterionic osmolytes

PCRs were carried out on a 1.2 kb fragment of human genomic DNA in the presence of silicon particles (approx: 0.5 mm×0.5 mm×0.3 mm) and 1 M betaine.

Lane 1: λ-BstEII marker; lanes 2–5: PCR (50 µl) carried out in buffer with water and different amounts of silicon particles: lane 2: 10 particles; lane 3: 50 particles; lane 4: 75 particles; lane 5: no particles as a control; lanes 6–9: PCRs (50 µl) carried out in buffer with 1 M betaine and different amounts of silicon particles: lane 6: 10 particles; lane 7: 50 particles; lane 8: 75 particles; lane 9: no particles as a control.

Figure 2:
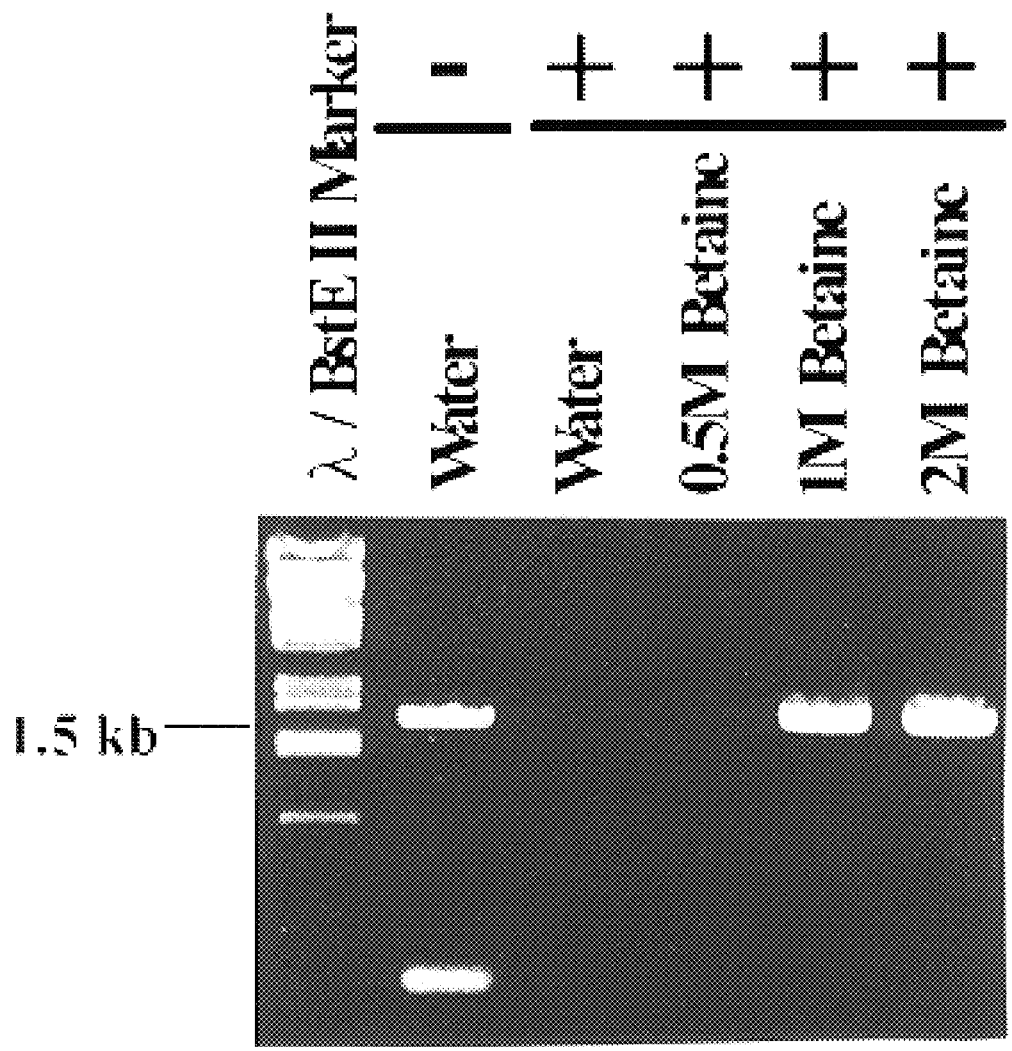

FIG. 2: PCR in the presence of silicon powder and zwitterionic osmolytes

PCRs were carried out on a 1.5 kb fragment of human genomic DNA in the presence of silicon powder and molar concentrations of betaine. Note that the PCRs in molar concentrations of betaine allow efficient and specific PCR amplification and reduce the inhibiting effect of silicon surfaces.

Lane 1: λ-BstEII marker; lane 2: PCR carried out in a standard PCR buffer without any silicon powder; lanes 3–6: PCR reaction carried out with 4.6 mg of silicon powder in 100 µl PCR volume; lane 3: water based buffer; lane 4: 0.5 M betaine; lane 5: 1 M betaine; lane 6: 2 M betaine.

The examples illustrate the invention.

EXAMPLE 1

PCR in the Presence of Silicon Particles and Zwitterionic Osmolytes

In this example it is shown that the inhibiting effect of inert surfaces such as pure silicon surfaces in a PCR as a nucleic acid template dependent reaction can be reduced with the presence of osmolytes such as betaine (in the examples glycine-betaine from Sigma was used).

Silicon is a very interesting material not only for the semiconductor technology but also for the biological field, since it is a material which can be easily handled and three dimensional micro-structures can be manufactured very rapidly. Therefore, experiments such as PCR in the presence of pure silicon are very important with a view of miniaturising biological processes on e.g. silicon wafers in the future. Pure silicon is generally known to inhibit biological processes such as PCRs for many reasons. One of these reasons is that the molecules interact with relatively large surfaces compared to the small volumes used in e.g. micro reaction chambers. To test the inhibiting effects of pure silicon surfaces in a PCR, PCR experiments on a 1.2 kb fragment of human genomic DNA cloned in a M13 vector in the presence of crushed silicon particles (approx: 0.5 mm×0.5 mm×0.3 mm) as a model system were carried out.

The reactions were prepared with 1 ng of M13 DNA in 1× buffer (10 mM Tris-HCl, pH 8.8 and 50 mM KCl) with increasing amounts (10, 50, 75) of silicon particles in water (FIG. 1, lanes 2–5) and 1 M betaine (FIG. 1, lanes 6–9)), 0.2 µM of each primer (M13–40 (24-mer): 5'-CGCCAGGGTTTTCCCAGTCACGAC-3'; (SEQ ID NO:1); M13-Rev (24-mer): 5'-TTTCACACAGGAAACAGCTATGAC-3'), (SEQ ID NO:2) 100 µM of each dNTP, 1.5 mM MgCl$_2$ and 2.5 Units of Taq DNA polymerase in a total volume of 50 µl. Reaction mixtures containing betaine were prepared by adding the required mixture of water and a 5 M stock solution of betaine to the final reaction volume of 50 µl.

The mixtures were cycled 30 times at 94° C. for 20 sec, 55° C. for 30 sec and at 73° C. for 2 min 30 sec. 1 µg of λ-BstEII digest was loaded on the gel as a marker. Further, 5 µl of the PCR products together with 2 µl gel loading solution (70% glycerol, 0.02 mg/ml bromphenol blue) were loaded on the agarose gels. The results (see FIG. 1) show that the inhibiting effect of increasing amounts of silicon particles can be overcome by adding betaine in molar concentrations to the PCR buffer.

EXAMPLE 2
PCR in the Presence of Silicon Powder and Zwitterionic Osmolytes In this example it is shown that the inhibiting effect of silicon powder in a PCR that was shown recently (Shoffner et al., loc. cit.) can be efficiently reduced by the presence of osmolytes such as the zwitterionic osmolyte betaine in the reaction buffer.

PCR experiments were carried out using a 1.5 kb fragment of human genomic DNA cloned in a M13 vector as a model system. The PCR with silicon were prepared with 4.6 mg of silicon powder (Sigma, 325 mesh, 99%, no. 21,561–9) in a final volume of 100 µl. This concentration of pure silicon powder was recently shown to inhibit PCRs (Shoffner et al., loc. cit).

PCRs were carried out in 1× buffer (10 mM Tris-HCl, pH 8.8 and 50 mM KCl) in water only (FIG. 2, lane 2) and 4.6 mg of silicon powder (FIG. 2, lanes 3–8) in water (FIG. 2, lanes 3), 0.5 M betaine (FIG. 2, lane 4), 1 M betaine (FIG. 2, lane 5), 2 M betaine (FIG. 2, lane 6), 1 ng M13 DNA, 0.3 µM of each primer (M13–40 (24-mer): 5'-CGCCAGGGTTTTCCCAGTCACGAC-3'; (SEQ ID NO:1) M13-Rev (24-mer): 5'-TTTCACACAGGAAACAGCTATGAC-3'), (SEQ ID NO:2) (200 µM of each dNTP, 1.5 mM MgCl$_2$ and 10 Units of Taq DNA polymerase in a total volume of 100 µl. Reaction mixtures containing betaine were prepared by adding the required mixture of water and a 5 M stock solution of betaine to the final reaction volume of 100 µl.

The mixtures were cycled 30 times at 94° C. for 20 sec, 55° C. for 30 sec and at 73° C. for 2 min 30 sec. 1 µg of λ-BstEll digest was loaded on the gel as a marker. Further, 5 µl of the PCR products together with 2 µl gel loading solution (70% glycerol, 0.02 mg/ml bromphenol blue) were loaded on the agarose gels.

What is claimed is:

1. A method for reducing or abolishing non-covalent interactions between an inert surface and a biological molecule, comprising adding a zwitterionic osmolyte of the structural formula:

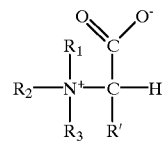

wherein R1, R2, and R3 are each selected from the group consisting of H, CH$_3$, C$_2$H$_5$ or any other alkyl, and R' is any amino acid residue, prior to or simultaneously with adding the biological molecule.

2. The method according to claim 1 wherein said zwitterionic osmolyte is selected from an amino acid or its methylation product.

3. The method according to claim 1 wherein said zwitterionic osmolyte is selected from betaine or glycine-betaine.

4. The method according to any one of claims 1, 2 or 3 wherein said osmolyte is present at a final concentration of 1 to 2.5 M.

5. The method according to any one of claims 1, 2 or 3 wherein said biological molecule is a macromolecule.

6. The method according to claim 5 wherein said macromolecule is selected from a carbohydrate, a polynucleic acid, a polypeptide or combinations or modifications thereof.

7. The method according to any one of claims 1, 2 or 3 wherein said biological molecule is selected from a peptide, an oligonucleotide or combinations or modifications thereof.

8. The method according to claim 7 wherein said polynucleic acid or oligonucleotide is DNA.

9. The method according to claim 7 wherein said polynucleic acid or oligonucleotide is RNA.

10. The method according to claim 7 wherein said inert surface is a silicon surface, a silicium wafer, a glass surface or combinations or chemical modifications thereof.

---

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
              DNA

<400> SEQUENCE: 1
cgccagggtt tcccagtca cgac                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
              DNA

<400> SEQUENCE: 2
tttcacacag gaaacagcta tgac                                           24

11. A kit comprising
(a) a concentrated stock solution of an osmolyte as specified in any of the preceeding claims;
(b) a reaction buffer formulation containing an osmolyte as specified in any of the preceeding claims; and/or
(c) an enzyme formulation containing an osmolyte as specified in any of the preceding claims.

12. A method for reducing or abolishing non-covalent interactions in a PCR reaction between an inert surface and a biological molecule, comprising adding a zwitterionic osmolyte of the structural formula:

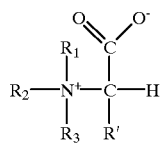

wherein R1, R2, and R3 are each selected from the group consisting of H, $CH_3$, $C_2H_5$ or any other alkyl, and R' is any amino acid residue, to the inert surface prior to or simultaneously with adding the biological molecule.

13. The method according to claim 12, wherein the biological molecule is an oligonucleotide.

14. The method according to claim 12, wherein the inert surface is a silicon surface, a silicium wafer, a glass surface or combinations or chemical modifications thereof.

15. The method according to claim 12, wherein the osmolyte is a betaine or glycine-betaine.

16. The method according to claim 12, wherein said zwitterionic osmolyte is selected from an amino acid or its methylation product.

17. The method according to any one of claims 12, 15 or 16 wherein the osmolyte is present at a final concentration of 1 to 2.5 M.

* * * * *